United States Patent [19]

Molina

[11] 4,049,568

[45] * Sept. 20, 1977

[54] NON-DRIPPING HEAT RESISTANT DYE PENETRANT

[75] Inventor: Orlando G. Molina, Westminster, Calif.

[73] Assignee: Rockwell International Corporation, El Segundo, Calif.

[*] Notice: The portion of the term of this patent subsequent to Oct. 28, 1992, has been disclaimed.

[21] Appl. No.: 580,442

[22] Filed: May 23, 1975

Related U.S. Application Data

[63] Continuation-in-part of Ser. No. 444,432, Feb. 21, 1974, Pat. No. 3,915,885, and Ser. No. 444,433, Feb. 21, 1974, Pat. No. 3,915,886, and a continuation-in-part of Ser. No. 521,730, Nov. 7, 1974, Pat. No. 3,939,092, and a continuation-in-part of Ser. No. 535,262, Dec. 23, 1974, Pat. No. 3,981,185.

[51] Int. Cl.² .................... C09K 11/06; G01N 19/08; G01N 21/16
[52] U.S. Cl. .............................. 252/301.19; 252/408; 73/104; 106/287 S; 250/302
[58] Field of Search ........................ 252/301.19, 408; 250/302; 23/230 R; 73/104; 106/287 S

[56] References Cited

U.S. PATENT DOCUMENTS

| | | | |
|---|---|---|---|
| 3,465,146 | 9/1969 | Molina | 252/301.19 X |
| 3,915,885 | 10/1975 | Molina | 252/301.19 |
| 3,915,886 | 10/1975 | Molina | 252/301.19 |
| 3,939,092 | 2/1976 | Molina | 252/301.19 |
| 3,939,101 | 2/1976 | Molina | 252/408 R |

*Primary Examiner*—John H. Mack
*Assistant Examiner*—Aaron Weisstuch
*Attorney, Agent, or Firm*—Charles T. Silberberg; L. Lee Humphries

[57] ABSTRACT

Biodegradable water washable dye penetrant composition in the form of a gel for use in non-destructive dye penetrant inspection of parts, and which can be applied to part surfaces at varying angles without dripping, and being resistant to decomposition and liquefaction when applied to heated surfaces, e.g. up to about 300° F, such composition consisting essentially of (1) an organic dye, preferably a fluorescent dye, (2) a carrier or solvent for said dye, in the form of a surfactant comprised of certain straight chain, primary, aliphatic oxyalkylated alcohols, particularly biodegradable surfactants comprised of the nonionic condensation products of linear primary aliphatic alcohols having from 10 to 18 carbon atoms, with ethylene oxide and propylene oxide, preferably in the form of a mixture thereof, such as the material marketed as Plurafac A-24, or in the form of certain ethoxylated secondary alcohols, particularly the biodegradable nonionic surfactants comprised of ethoxylates of a mixture of secondary alcohols having linear alkyl chains of from 11 to 15 carbon atoms, and (3) silica, particularly fumed silica, such silica employed e.g. in a proportion of 5 parts per 1 part of the sum of the other dye penetrant components, including biodegradable surfactant and dye, by volume.

16 Claims, No Drawings

NON-DRIPPING HEAT RESISTANT DYE PENETRANT

This application is a continuation-in-part of my co-pending applications Ser. Nos. 444,432 and 444,433, both filed Feb. 21, 1974, now U.S. Pat. Nos. 3,915,885 and 3,915,886; 521,730, filed Nov. 7, 1974, now U.S. Pat. No. 3,939,092; and 535,262, filed Dec. 23, 1974, now U.S. Pat. No. 3,981,185.

BACKGROUND OF THE INVENTION

This invention relates to an improved non-dripping, heat resistant biodegradable dye penetrant composition and method for non-destructively testing material specimens to locate and identify surface voids, cracks or defects. The invention is especially concerned with a novel dye penetrant composition having the above characteristics, and which can be applied to heated surfaces of an object without decomposition or liquefaction, and without generating fumes, and which in addition has the properties of being readily water washable, and sensitive for disclosing a wide range of defective conditions in parts, employing as solvent or vehicle certain biodegradable nonionic surfactants in the form of certain oxyalkylated alcohols, and mixtures thereof; and to a method of utilizing such dye penetrant composition for non-destructive testing of parts, particularly parts heated to elevated temperature.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, as well as intermediate size and gross cracks, it is necessary that the dye penetrant composition have high sensitivity.

In addition, stability of the penetrant solution is essential without the necessity for carefully balancing the various liquid components of a dye penetrant solution in order to obtain efficient penetration of the solution into the cracks and flaws of a part, dye solubility, wetting action and washability control.

An additional criterion has recently developed also with respect to dye penetrant solutions and compositions. Generally, dye penetrant solutions presently being used and containing solvents and wetting agents present a disposal problem in that they are substantially non-biodegradable, that is, they are very difficult to decompose by bacteria in sewage disposal plants. Hence the necessity for the development of dye penetrant solutions and compositions which are biodegradable, that is which employ dye solvents and carriers which are biodegradable, and are readily available despite the petrochemical shortage, has attained considerable importance.

In my above U.S. Pat. Nos. 3,915,885 and 3,915,886 there is disclosed novel dye penetrants which have improved washability and sensitivity characteristics, and which are biodegradable, containing as the vehicle for the dye, certain biodegradable nonionic oxyalkylated alcohols.

Further, penetrant inspection of hot surfaces of parts, especially those of overhead and vertical orientation, present a particular problem. Conventional penetrants when employed under these conditions become extremely liquefied, produce obnoxious fumes, drip and change in sensitivity due to loss of volatiles. A conventional dye penetrant employed under these conditions and thinned by the action of heat creates a messy condition because it cannot be contained in prescribed areas of parts or assemblies being inspected.

In my U.S. Pat. No. 3,465,146 there is disclosed a dye penetrant which comprises conventional liquid organic dye carriers or vehicles such as N-methyl-2-pyrrolidone, and a thickening agent such as silica. However, although such composition is effective when applied to surfaces which are at approximately ambient temperature, when applied to heated surfaces, e.g. surfaces heated at temperature in excess of about 100° F, the composition dries and forms a powdery material and fails to perform effectively. In addition, the dye penetrant compositions of this patent are not biodegradable.

Accordingly, an object of the present invention is the provision of a biodegradable heat resistant dye penetrant composition which is a simple formulation and which does not require the use of mixtures of conventional solvents and wetting agents, and which is formed of an essentially single or sole vehicle or carrier for the dye in the form of a biodegradable nonionic surfactant, and which is heat stable, has excellent sensitivity and is essentially non-flammable and non-toxic. A particular object of the invention is to provide a dye penetrant composition of the above noted type, and which incorporates an additive which converts the dye penetrant composition to a gel-like consistency, permitting the dye penetrant composition to be applied to heated surfaces of objects disposed at varying angles, without becoming liquefied and dripping, and without generating obnoxious fumes, substantially without affecting the biodegradability, penetrability or sensitivity of the dye penetrant. A still further object is the provision of procedure employing such novel heat stable biodegradable dye penetrant composition for inspection of cracks, flaws and metallurgical conditions in structural components, particularly parts heated to elevated temperature, without dripping.

DESCRIPTION OF THE INVENTION

According to the present invention, it has been found that the above objects and advantages can be accomplished and an improved heat resistant and non-dripping dye penetrant, having good sensitivity for detection of cracks and defects in metal surfaces, and which is biodegradable, is provided by employing as a solvent or carrier for the dye, e.g. fluorescent dye, a surfactant in the form of certain biodegradable nonionic surfactants comprised of certain oxyalkylated linear alcohols, of the types disclosed in my above U.S. Pat. Nos. 3,915,885 and 3,915,886 separately or in admixture, and incorporating a substantial proportion of silica (silicon dioxide), preferably in powdered form. Upon incorporation of the powdered silica into the dye penetrant containing the above noted nonionic surfactant as carrier, and dye, the resulting composition is essentially in the form of a gel which can range in consistency from thin cream-like gels to heavy grease-type gels, depending particularly upon the proportion of silica incorporated.

The resulting dye penetrant composition or gel of the invention avoids the above noted problems previously encountered in employing dye penetrants on heated surfaces, in that the gel-type dye penetrants of the invention are resistant to liquefaction and decomposition and do not generate fumes when applied to surfaces heated to a temperature, e.g. above 100° F. In view of such heat stability, the dye penetrant composition when applied to slanted or angularly disposed heated surfaces, including overhead and vertical heated surfaces, of objects to be nondestructively tested, does not drip, run off or puddle. Moreover, the silica additive is not only heat resistant but is inert with respect to the other components of the dye penetrant composition, and the excess dye penetrant can be readily washed away, the composition other than the inert silica, being biodegradable. Of particular significance, the presence of the silica in the dye penetrant composition does not change the sensitivity or brillance of the dye indication of cracks and flaws which are obtained.

It was unexpected to find that the dye penetrant composition of the invention containing silica is heat resistant at temperatures up to about 300° F for extended periods of time, whereas the dye penetrant composition of my above patent, and containing particularly N-methyl-2-pyrrolidone as vehicle, is not heat resistant and becomes powdery and ineffective under such conditions, while the washability, sensitivity and fluorescent brilliance of the dye penetrant composition of the invention on the other hand is not adversely affected by exposure to such elevated temperature use.

The above advantageous characteristics of the dye penetrant composition of the invention are particularly valuable for inspection of parts or components of any equipment which is under continuously heated conditions and cannot be shut down conveniently, such as steam generators and atomic reactors, or parts with thick cross sections, e.g. welds in shipbuilding, which would require a considerable time for cooling before nondestructive test inspection. Also, the invention composition can be employed on parts which are environmentally heated, such as by solar heating.

The nonionic biodegradable solvent or carrier employed essentially as the sole vehicle or carrier for the dye of the dye penetrant composition according to the invention can be alkylene oxide condensation products prepared by the reaction of an organic compound having a reactive hydrogen atom, such as an aliphatic alcohol, with ethylene oxide, propylene oxide, or mixtures thereof. More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One class of nonionic carriers within the broad class of materials defined above is a cogeneric mixture of compounds represented by the formula:

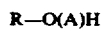

R—O(A)H wherein:

R is an essentially linear alkyl group having from 10 to 18 carbon atoms, with the proviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetra-decyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The above nonionic biodegradable surfactants employed as carrier or vehicle for the dye of the penetrant solution according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixtures being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain. This cogeneric mixture of condensation products and the method of their preparation are disclosed in U.S. Pat. No. 3,340,309, and such disclosure is also incorporated herein by reference. The nonionic oxyalkylated alcohols marketed as the "RA-20" grades of Plurafac, are believed representative of the class of surface active agents disclosed in the latter patent.

Various other Plurafac grades which are marketed and are believed to be generally within the above-described classes of oxyalkylated alcohol surfactants are those designated RA-43, A-24, A-25, B-25-5, B-26 and D-25.

A class of particularly preferred nonionic biodegradable solvents or carriers which can be employed as substantially the sole vehicle for the dye of the dye penetrant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as carrier for the dye penetrant of the invention is a mixture of compounds which can be represented by the formula:

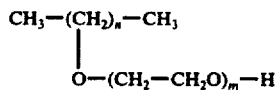

where $n$ is in the range from 9 to 13, and $m$ is an average of 3 to 12.

Although preferably each of the immediately above-defined surfactants is formed of a mixture of two or more linear alkyl hydrophobic chains ranging from $C_{11}$ to $C_{15}$ as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a $$-\underset{|}{C}H- \text{ group.}$$

Such hydrophilic polyoxyethylene chain is generally expressed in terms of an average number of moles of ethylene oxide.

Illustrative examples of biodegradeable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

Tergitol 15-S-3
" 15-S-5
" 15-S-7
" 15-S-9 " 15-S-12

In each case of the Tergitol S series of surfactants listed above, the number to the left of the S indicates a hydrophobic aliphatic chain of from 11 to 15 carbon atoms derived from a mixture of alcohols on $C_{11}$ to $C_{15}$ backbone chains, and the number to the right of the S designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3; a mixture of 15S-3 and 15-S-9; and a mixture of 15-S-5 and 15-S-9.

The above preferred class of nonionic biodegradeable surfactants employed as carrier or vehicle for the dye of the penetrant solution according to the invention, are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above preferred nonionic surfactants in the form of ethoxylates of linear secondary aliphatic alcohols, is described in U.S. Pat. No. 2,870,220.

Any suitable dye generally employed in dye penetrant compositions can be incorporated into the nonionic oxyalkylated alcohol surfactants described above for producing the dye penetrant compositions employed in the invention process. Preferably, however, a fluorescent dye is employed for this purpose. The oxyalkylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention preferably contains a fluorescent dye. Various types of fluorescent dyes can be employed including for example the dye marketed as Fluorol 7GA as well as other fluorescent dyes such as those marketed as Calcofluor Yellow, Azosol Brilliant Yellow 6GF; Rhodanine B, Rhodanine 6 GDN, Calcofluor White RW, Blancophor White AW, Auramine and Eosine G, and water soluble fluorescent dyes such as Blancopher FFG.

The dye penetrant composition employed according to the invention alternatively can contain non-fluorescent or daylight type dyes such as azo type dyes, e.g., xylenaezobeta-naphthol, Mefford No. 322 dye, believed to be o-tolueneazoxyleneazo-beta-naphthol, and the azo dyes marketed as Oil Red "0" and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The amount of dye which is incorporated into the oxyalkylated alcohol surfactant or carrier to produce the dye penetrant composition of the invention, can range from about 0.1 to 15, preferably about 0.5 to about 10, parts of the dye, or mixtures thereof, per 100 parts of the oxyalkylated alcohol surfactant, by weight. In preparing the dye penetrant composition employed according to the invention, the dye is simply added to the oxyalkylated alcohol carrier, in the desired proportion. The resulting dye penetrant composition has both high and low temperature stability.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility for production of dye penetrants having high sensitivity according to the invention, when employed in combination with the other water washable and water soluble Tergitols such as Tergitol 15-S-5 and Tergitol 15-S-9. Also, particularly effective dye penetrants are provided according to the invention employing a combination or mixture of the above Tergitols 15-S-5 and 15-S-9, and to which there can be added optionally Tergitol 15-S-3, as described in my above U.S. Pat. No. 3,959,092.

The silica additive incorporated in the dye penetrant composition for rendering such composition heat resistant and nondripping, is preferably in fine powder form and of particle size ranging from about 0.007 to about 0.050 micron (about 70 to about 500 Angstroms), and is an extremely fluffy, snow-white powder of extremely low bulk density. A commercially available form of this component is marketed as Cab-O-Sil M-5 by Cabot Corporation. The Cab-O-Sil has an enormous external area, one gram of Cab-O-Sil M-5 having about 400 square meters of surface area. Cab-O-Sil M-5 is a submicroscopic fire-dry fumed silica different in structure from precipitated silicas or silica gels with a maximum density of 2.3 lbs./cu.ft.

The silica thus incorporated into the dye penetrant hereof is capable of conferring thickening properties on the liquid dye penetrant, without increasing the viscosity thereof. The formation of the resulting gel does not inhibit the penetrability or sensitivity of the gelled penetrant, but only limits its ability to flow over the surface to which it is applied. Thus, the silica in the gel functions merely to entrap the penetrant in a multitude of sponges formed by the silica particles, but the penetrant itself remains liquid and quickly spreads into any surface defect with which the dye penetrant gel comes in contact in the same manner that a sponge filled with water wets a surface. The silica additive however is chemically stable and completely inert with respect to both the dye and the oxyalkylated nonionic surfactant vehicle of the penetrant. Thus, the liquid vehicle of the penetrant remains in liquid form and its penetrability and sensitivity are not affected by addition of the silica additive.

As previously noted, by addition of the silica, the consistency of the previously highly mobile liquid dye penetrant changes to a gel-like appearance with the additive holding the liquid penetrant in the location where it is applied, preventing the tendency of the liquid to drip or flow over a vertical or slanted surface, while the penetrant itself remains liquid and spreads quickly into any surface defect with which the dye penetrant gel comes into contact.

The amount of silica added to the dye penetrant can vary widely, but generally the silica is a substantial portion of the resulting composition, the amount employed being sufficient to convert the dye penetrant composition into a gel. Generally, there can be employed about 1 to about 8 parts of silica per 1 part, by volume, of the sum of the other components of the dye penetrant, namely the oxyalkylated nonionic surfactant and dye. Preferably about 1 to about 6 parts of silica, and most desirably about 3 to about 6 parts of silica, to 1 part, by volume, of the sum of the remaining dye penetrant components, is utilized. The above general and preferred volumetric ranges correspond approximately to a general range of about 4 to about 32, and a preferred range of about 4 to about 25, parts of silica, to 100 parts by weight, of the sum of the surfactant and dye. When smaller proportions of silica are employed within the above noted ranges, the resulting gels can have a thin cream-like consistency, and when larger proportions of silica are employed within the above noted ranges, the resulting gels can have a heavy grease-type consistency. The gels produced according to the invention are generally clear and translucent. Regardless of the consistency of such gels, it has been found that they are sufficiently adhesive to prevent runoff of the dye penetrant when applied to slanted, vertical or overhead surfaces.

Typical liquid dye penetrant compositions to which the silica additive can be added according to the invention are as follows:

TABLE 1

| COMPONENTS | Liquid Compositions (Parts by Weight) | | | | | | | |
|---|---|---|---|---|---|---|---|---|
| | A | B | C | D | E | F | G | H |
| Tergitol 15-S-3 | — | — | — | — | 25 | — | — | — |
| Tergitol 15-S-5 | 100 | — | 75 | — | 75 | — | 75 | 75 |
| Tergitol 15-S-9 | — | — | 25 | — | — | 100 | 25 | 25 |
| Pluravac A-24 | — | 100 | — | — | — | — | — | — |
| Plurafac RA-43 | — | — | — | 100 | — | — | — | — |
| Calcofluor White RW | 5.0 | 5.0 | 5.0 | 5.0 | 2.5 | 2.5 | 2.5 | 1.25 |
| Fluorol 7 G A | 1.5 | 1.5 | 1.5 | 1.5 | 0.75 | 0.75 | 0.75 | 0.375 |

Illustrative examples of the dye penetrant gel compositions of the invention incorporating varying proportions of the fumed silica, Cab-O-Sil M-5, into the typical dye penetrant compositions A-H of Table 1 above, are set forth in Table 2 below.

TABLE 2

| COMPONENTS | Dye Penetrant Gel Compositions (Parts by Volume) | | | | | | | | |
|---|---|---|---|---|---|---|---|---|---|
| | I | II | III | IV | V | VI | VII | VIII | IX |
| Cab-O-Sil M-5 | 5 | 5 | 4 | 3 | 2 | 1 | 6 | 5 | 7 |
| A | | 1 | | | | | | | 1 |

TABLE 2-continued

| COMPONENTS | Dye Penetrant Gel Compositions (Parts by Volume) | | | | | | | | |
|---|---|---|---|---|---|---|---|---|---|
| | I | II | III | IV | V | VI | VII | VIII | IX |
| B | | 1 | | | | | | | |
| C | | | 1 | | | | | | |
| D | | | | 1 | | | | | |
| E | | | | | 1 | | | | |
| F | | | | | | 1 | | | |
| G | | | | | | | 1 | | |
| H | | | | | | | | 1 | |

Where a developer composition is employed, any one of the three general types of developer compositions, namely, dry powder, wet aqueous (water-base) and wet non-aqueous (volatile solvent base) developer compositions can be employed. In each case, the developer composition contains a light colored powder, forming a coating which contrasts with the color of the dye in the penetrant and which acts as a wick or blotter, and causes liquid penetrant containing the dye, e.g. fluorescent dye, which was retained in the cracks or surface flaws, to be drawn up out of the surface defects by capillary action and to bleed through the powder. Preferred developer compositions for use in conjunction with the dye penetrant composition according to the invention, are those described in my U.S. Pat. No. 3,803,051, which is a dry powder developer containing fumed alumina, fumed silica, fumed titanium dioxide and talc, and in my U.S. Pat. No. 3,748,469, which is a wet nonaqueous developer composition consisting essentially of isopropyl alcohol, talc and glycol monobutyl ether. The descriptions of such developer compositions contained in the above patents are incorporated herein by reference.

The dye penetrant composition employed in the invention process, employing the above biodegradable nonionic oxyalkylated alcohol surfactants can be tailored to have varying degrees of sensitivity for detection of the smallest microcracks to gross cracks in a part surface by generally varying the amount of dye incorporated and also by selecting particular surfactants or combinations thereof.

In the method for detecting cracks and flaws in the surface of an object employing the dye penetrant compositions of the invention, such dye penetrant in gel form is applied to the part surface in any suitable manner, as for example, by brushing. After application of the dye penetrant gel to the surface of the test part, the excess dye penetrant composition is readily removed from the object surface by water washing, e.g. by application of a water spray or sprayed mixture of air and water. In such procedure when the part surface is at high temperature of the order of about 200°-300° F, some of the water wash is converted to steam, which is beneficial. The dye penetrant gel compositions hereof, such as those containing the above noted Plurafacs and particularly those containing the above Tergitols 15-S-5 to 15-S-9, generally have excellent washability without removing dye penetrant from the cracks and defects on the part surface.

If desired, a developer composition of the types noted above can then be applied to the part surface followed by removal of excess developer, as by means of an air blast. The part is then viewed under suitable lighting conditions, employing black light or fluorescent illumination when the dye penetrant contains a fluorescent dye.

Illustrative examples of practice of the invention are set forth below.

EXAMPLE 1

Dye penetrant composition I of Table 2 above was prepared by mixing 5 parts of Cab-O-Sil M-5 to 1 part by volume of the liquid dye penetrant composition A of Table 1. The resulting formulation was a heavy grease-type gel.

A test panel of 2014 aluminum containing microcracks uniformly distributed over the panel was divided by a groove into two equal test areas for test comparison purposes. The fluorescent dye penetrant gel composition I prepared as noted above was applied as by brushing to one half of the surface of the test panel which was previously heated to about 300° F for a period of 3 hours. The excess dye penetrant gel composition on the test panel was removed by an air-water spray applied over the coating, causing almost instantaneous washing away of the dye penetrant gel from the surface of the panel without dislodging liquid dye penetrant from the surface cracks and thus entrapping the penetrant therein. The part was then dried by an air blast.

The procedure above was repeated, but applying the liquid dye penetrant composition A of Table 1 above containing no silica, to the other half of the test panel surface, followed by application of a water wash under the same conditions noted above for removal of excess dye penetrant, and finally followed by drying with an air blast.

The dye penetrant liquid removed from the part surface in each of the above procedures was biodegradeable.

Inspection of the two penetrant treated surfaces of the test panel under ultraviolet or fluorescent light, revealed fluorescent indications from numerous readily defined microcracks therein, the fluorescent indications on both sides of the test panel being in substantially equivalent concentration, with substantially the same brightness and sensitivity or optical intensity on both sides of the test panel.

This example shows that silica containing dye penetrant composition of the invention, following removal of excess dye penetrant gel, has essentially the same sensitivity or ability to disclose cracks and defects in a part surface, and has the same biodegradability as in the case of the dye penetrant composition free of silica.

EXAMPLE 2

The gel compositions I and II of Table 2 above, each containing 5 parts of Cab-O-Sil M-5, to 1 part of the liquid dye penetrant compositions A and B, respectively of Table 1 above, were formulated, both being heavy grease-type gels which were clear and translucent.

Both of these gel penetrants were applied to test panels of chromium-plated brass containing minute cracks of the order of 0.00002 to 0.0001 inch in width, closely distributed over their entire surfaces.

The gel compositions I and II each were applied by brushing to a series of test panels of the above type, such test panels being placed in various positions including slanted and vertical positions in a heated air circulating type oven. The tests were conducted at various temperatures and time cycles ranging from 100° F for 3 hours to 300° F for 3 hours.

It was noted that the gel compositions remained on the areas of the test panels to which the compositions were applied, without any dripping or runoff, and no fumes were generated during the period that the gels were on the panels.

The test panels were then sprayed with clean water or wiped with clean water-soaked rags to remove surface excess penetrant, followed by air blasting for drying.

The test panels were then immersed in a powder developer having the following composition, according to my above U.S. Pat. No. 3,083,051.

| COMPONENTS | PERCENT BY WEIGHT |
|---|---|
| Talc | 52 |
| Alumina | 35 |
| Silica | 4 |
| $TiO_2$ | 9 |

Excess developer composition was then carefully removed from the surfaces of the test panels by means of a gentle air blast.

The panels were then placed under black light (fluorescent) illumination and viewed. It was observed that the surfaces of all panels to which the above gel compositions I and II were applied, disclosed fluorescent indications from numerous readily defined microcracks therein, such fluorescent indications being sharp and brilliant and revealing all defective conditions on the surface of the test panels.

The results of these tests showed the two gel penetrant formulations I and II each containing respectively Tergitol nonionic 15-S-5 and Plurafac A-24 nonionic surfactants, and the fumed silica, to be highly heat resistant, non-migrating, non-liquefying formulations, and performing effectively under the drastic heated environment employed in the tests.

EXAMPLE 3

The grease-type dye penetrant composition of above U.S. Pat. No. 3,465,146 corresponding to composition I above, but containing N-methyl-2-pyrrolidone as liquid vehicle for the dye instead of Tergitol 15-S-5, was tested by application to test panels of the type employed in Example 2 and heated under the same temperature conditions as in Example 2.

After the period of heating, it was noted that the initially grease-like penetrant compositions applied to the surface of such panels had dried out and formed a powdery material.

Such powdery material was removed from the panel surfaces, a developer applied as in Example 2, and following removal of such developer the panels were veiwed under fluorescent light. It was found that unsatisfactory results were obtained, which did not provide the sensitivity, concentration and brilliance of the fluorescent indications which were observed on the test panels according to the procedure of Example 2 employing the gel compositions I and II above.

EXAMPLE 4

Tests were carried out following the procedure of Example 2 above, but employing test compositions corresponding to compositions I and II above, wherein the proportion of Cab-O-Sil M-5 varied from 1 to 4 parts, to 1 part of the respective dye penetrant liquids A and B. The formulations thus produced ranged from thin cream-like gels employing the smaller proportions of the silica, to heavy grease-type gels when employing the higher proportions of silica, the gels in each case being essentially clear and translucent.

As in the case of Example 2, the gelled penetrants remained on the surface of the variously positioned and heated panels without dripping, runoff or puddling.

Following removal of the excess dye penetrant from the surface of the test panels, the remaining liquid dye penetrants thus removed were biodegradable.

In all cases the dye penetrant composition performed excellently with bright fluoresecent indications of the microcracks obtained.

The dye penetrant gel compositions of the invention are particularly applicable for use in detecting cracks, defects and metallurgical conditions in assemblies and parts which have been heat treated and are still hot, recently welded assemblies and parts, aircraft stationed in hot climates, rocket engines which are still hot, atomic reactors which require penentrant inspection while in extremely heated condition, and geothermal pressure vessels and piping.

From the foregoing, it is seen that the invention provides a highly effective substantially biodegradable water washable dye penetrant composition in the form of a gel, which is heat resistant, nonflammable, and non-toxic, and which can be applied effectively to heated surfaces of parts positioned at various angles, without runoff or dripping, and which can be readily removed from a part surface by conventional washing. The dye penetrant gels of the invention contain as essential components a single carrier for the dye, which is preferably fluorescent, in the form of certain biodegradable oxyalkylated alcohols, and a substantial or major proportion of a silica, preferably fumed silica. Following removal of excess gel penetrant from the surface of the parts and further processing of the part surfaces in the conventional manner for viewing under suitable, e.g. fluorescent, lighting conditions, fluorescent indications of high brilliance, definition and resolution of the dye traces from cracks and flaws in the part surfaces are obtainable, equivalent in this respect to the results obtained employing the same dye penetrant but in the absence of the silica.

Since various changes and modifications of the invention will occur to and can be made readily by those skilled in the art without departing from the invention concept, the invention is not to be taken as limited except by the scope of the appended claims.

What is claimed is:

1. A heat resistant biodegradable dye penetrant composition for use in non-destructive testing for detecting cracks and flaws and metallurgical conditions in the surface of an object, which comprises (1) a biodegradable nonionic surfactant selected from the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide, (2) a small amount of dye based on said surfactant and soluble in said surfactant, said dye being present in an amount ranging from about 0.1 to 15 parts, per 100 parts, by weight of said surfactant, and (3) an amount of silica sufficient to convert said dye penetrant composition into a gel.

2. A dye penetrant composition as defined in claim 1, said silica being present in an amount ranging from about 1 to about 8 parts, to 1 part by volume of the sum of said surfactant and said dye.

3. A dye penetrant composition as defined in claim 1, and said silica being powdered silica present in an amount ranging from about 1 to about 6 parts, to 1 part by volume of the sum of said surfactant and said dye.

4. A dye penetrant composition as defined in claim wherein said silica is fumed silica.

5. A dye penetrant composition as defined in claim 3, wherein said dye is a fluorescent dye.

6. A dye penetrant composition as defined in claim 1, wherein said surfactant is the sole liquid carrier for said dye.

7. A dye penetrant composition as defined in claim 1, wherein said surfactant (a) is a mixture of compounds having the formula:

$$R - O(A)H$$

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxyprolene to oxyethylene ratio of said total weight being from 0.85:1 to 2.75:1; and wherein said surfactant (b) is ethoxylates of a mixture of alcohols having the formula:

$$CH_3-(CH_2)_n-CH_3$$
$$|$$
$$O-(CH_2-CH_2O)_m-H$$

where $n$ is in the range from 9 to 13 and $m$ is an average of 3 to 12, said composition being substantially non-flammable.

8. A dye penetrant composition as defined in claim 7, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains through the ether linkage, and wherein said surfactant (b) is selected from the group consisting of said ethoxylates of said mixture of alcohols, wherein $n$ ranges from 9 to 13, and $m$ is an average of 3, 5, 7, 9 or 12.

9. A dye penetrant composition as defined in claim 8, said silica being present in an amount ranging from about 1 to about 8 parts, to 1 part by volume of the sum of said surfactant and said dye.

10. A dye penetrant composition as defined in claim 8, said silica being powdered silica present in an amount ranging from about 1 to about 6 parts, to 1 part by volume of the sum of said surfactant and said dye.

11. A dye penetrant composition as defined in claim 10, wherein said dye is a fluorescent dye, and said silica is fumed silica, said dye penetrant composition ranging from a thin cream-like gel to a heavy grease-type gel, said dye penetrant composition being non-dripping.

12. A dye penetrant composition as defined in claim 8, wherein said surfactant is said surfactant (b).

13. A dye penetrant composition as defined in claim 12, wherein said dye is a fluorescent dye, said silica is fumed silica, and said silica is present in an amount ranging from about 1 to about 6 parts, to 1 part by volume of the sum of said surfactant and said dye.

14. A dye penetrant composition as defined in claim 13, wherein said silica is present in an amount ranging from about 3 to about 6 parts, to 1 part by volume of the sum of said surfactant and said dye.

15. A dye penetrant composition as defined in claim 13, employing a combination of said biodegradable nonionic surfactants.

16. A dye penetrant composition as defined in claim 13, employing a combination of said biodegradable nonionic surfactants wherein $m$ in one of surfactants is an average of 5 and $m$ in another of said surfactants is an average of 9.

* * * * *